(12) United States Patent
Weisshaupt

(10) Patent No.: US 6,460,700 B2
(45) Date of Patent: Oct. 8, 2002

(54) CARTRIDGE FOR RECEIVING CLIPS

(75) Inventor: Dieter Weisshaupt, Immendingen (DE)

(73) Assignee: Aesculap AG & Co. KG, Tuttlingen (DE)

( * ) Notice: Subject to any disclaimer, the term of this patent is extended or adjusted under 35 U.S.C. 154(b) by 0 days.

(21) Appl. No.: 09/917,869

(22) Filed: Jul. 26, 2001

(65) Prior Publication Data

US 2002/0017472 A1 Feb. 14, 2002

Related U.S. Application Data

(63) Continuation of application No. PCT/EP99/10370, filed on Dec. 24, 1999.

(30) Foreign Application Priority Data

Jan. 30, 1999 (DE) .......................................... 199 03 752

(51) Int. Cl.⁷ .............................................. B65D 85/24
(52) U.S. Cl. ...................................... 206/339; 206/340
(58) Field of Search ................................ 206/338–341, 206/363, 370, 438; 606/151, 157, 158

(56) References Cited

U.S. PATENT DOCUMENTS

| | | | | |
|---|---|---|---|---|
| 4,212,390 A | * | 7/1980 | Raczkowski | 206/339 |
| 4,361,229 A | * | 11/1982 | Mericle | 206/339 |
| 4,696,396 A | * | 9/1987 | Samuels | 206/339 |
| 4,936,447 A | * | 6/1990 | Peiffer | 206/339 |
| 4,961,499 A | * | 10/1990 | Kulp | 206/339 |
| 4,972,949 A | * | 11/1990 | Peiffer | 206/339 |
| 5,201,416 A | * | 4/1993 | Taylor | 206/339 |
| 5,908,430 A | * | 6/1999 | Appleby | 206/339 |
| 6,158,583 A | * | 12/2000 | Forster | 206/339 |

* cited by examiner

Primary Examiner—Jim Foster
(74) Attorney, Agent, or Firm—Barry R. Lipsitz

(57) ABSTRACT

In order to reliably configure the positioning of the clip in the cartridge in any phase, even during removal, in the case of a cartridge for receiving U-shaped clips having a web and two arms projecting therefrom, with a support abutting the underside of the web and with clamping members, which abut the web laterally at least on one side and are elastically removable from this web transversely to the plane of the clip, it is proposed that additional clamping members are provided, which abut the arms laterally at least on one side and are elastically removable from these arms transversely to the plane of the clip, and which are pressed elastically against the arms independently of the clamping members abutting the web.

17 Claims, 3 Drawing Sheets

Figure 1:
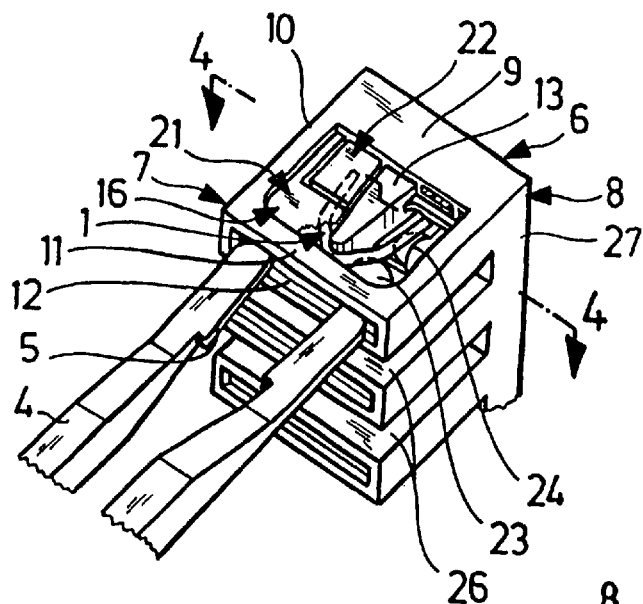

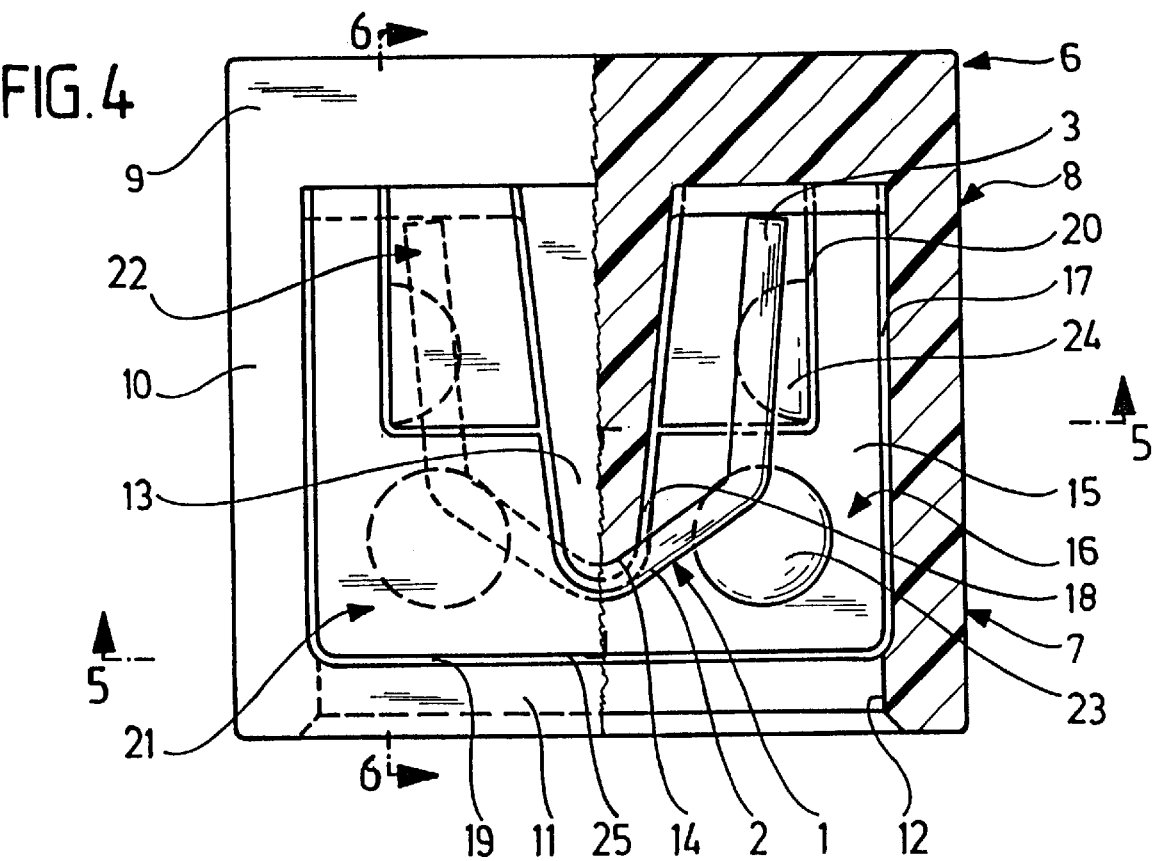
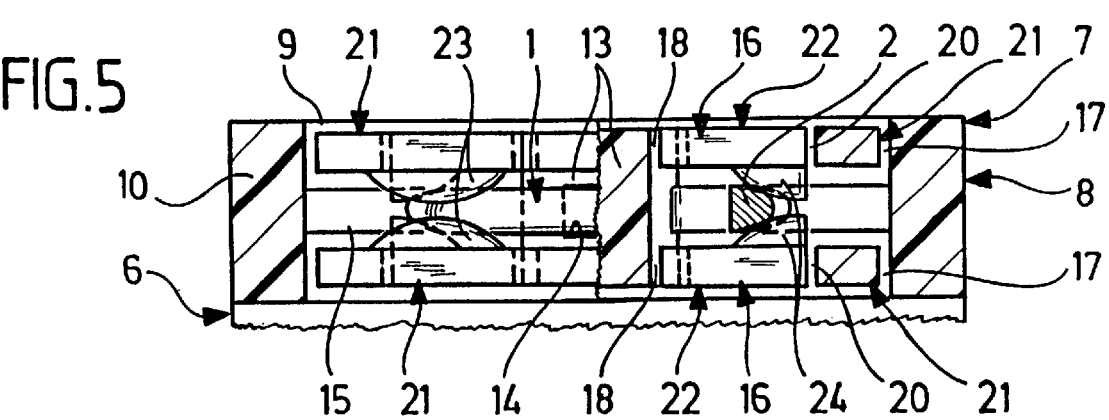
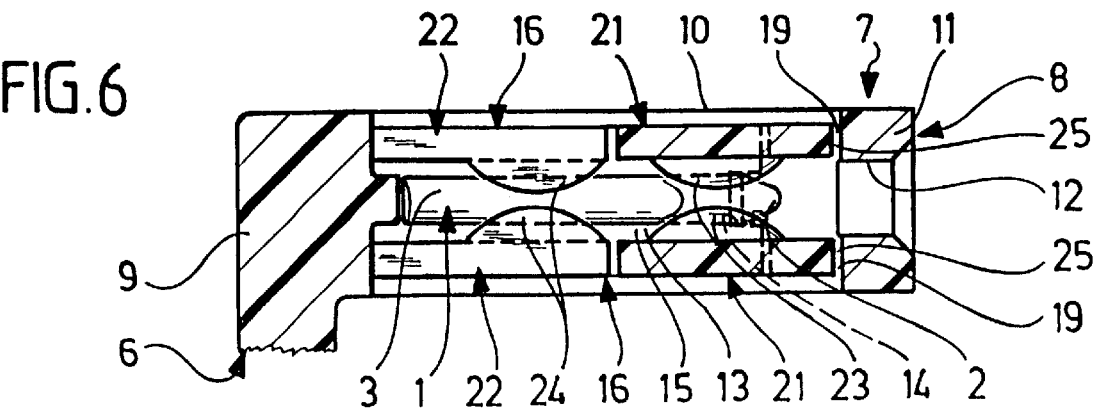

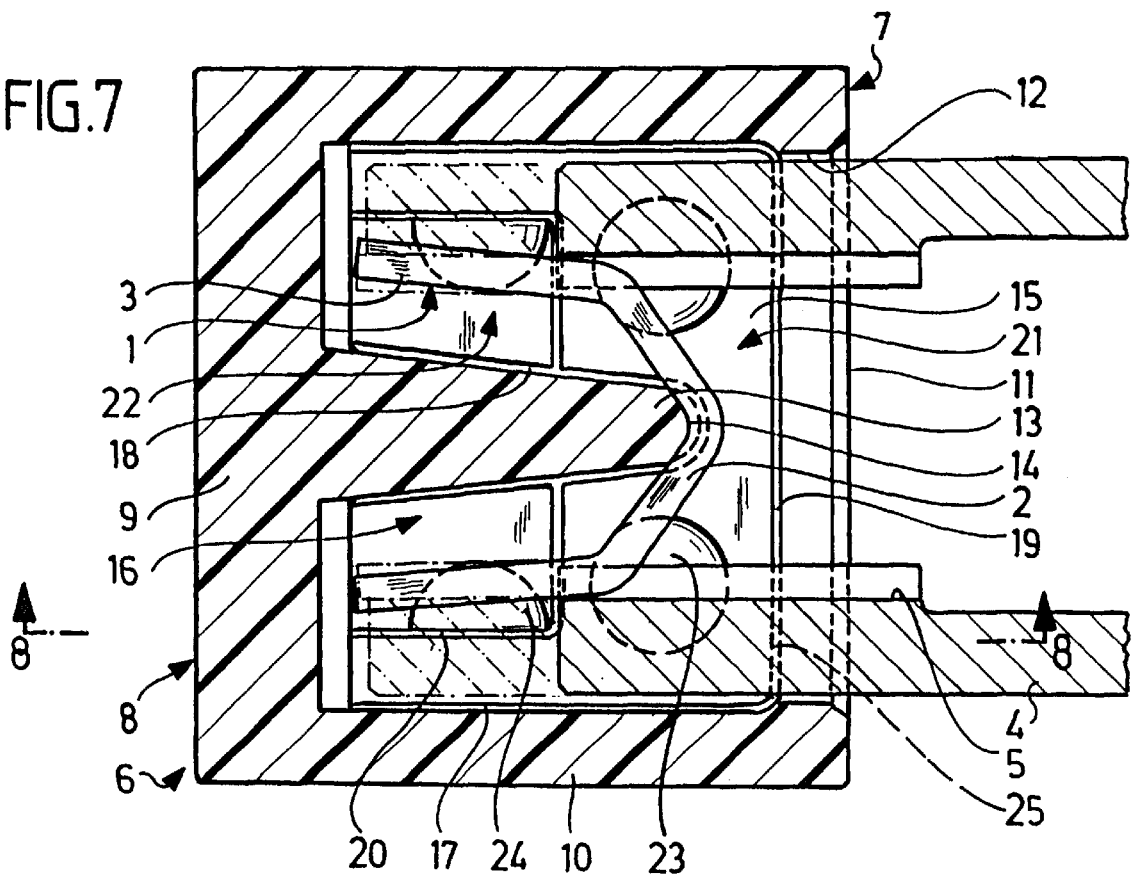
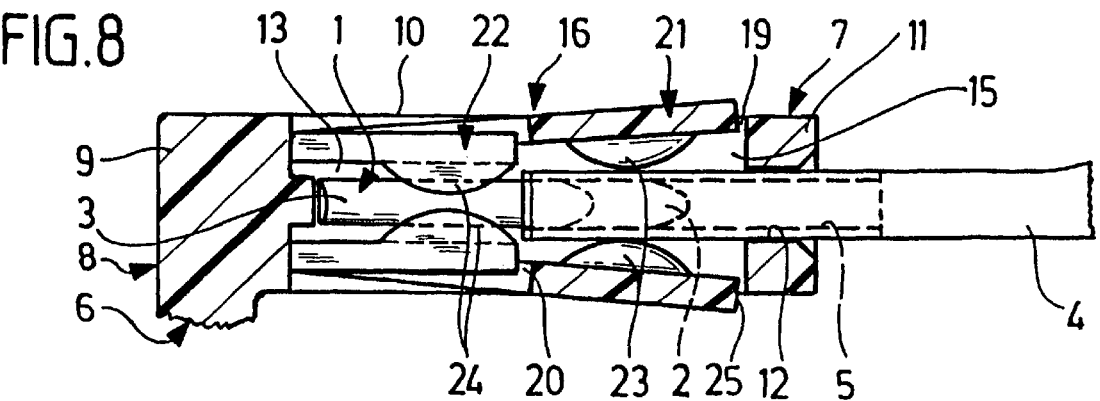
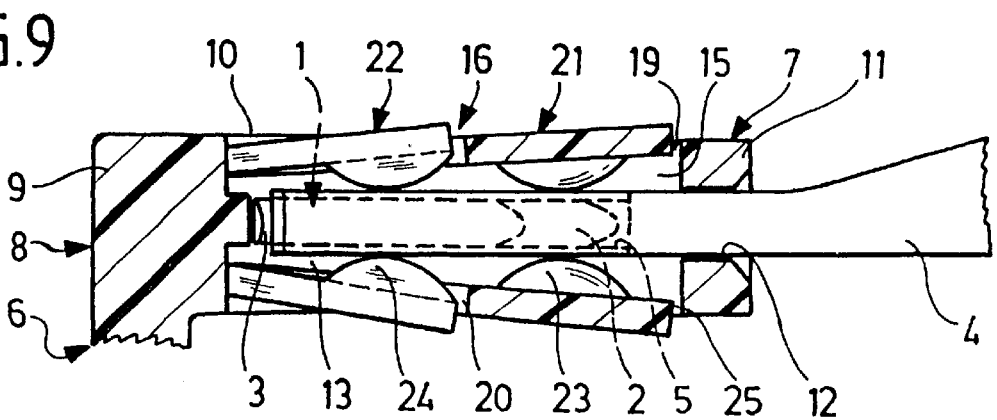

CARTRIDGE FOR RECEIVING CLIPS

This is a continuation of PCT/EP99/10370, filed Dec. 12, 1999.

The invention relates to a cartridge for receiving U-shaped clips having a web and two arms projecting therefrom, with a support abutting the underside of the web and with clamping members, which abut the web laterally at least on one side and are elastically removable from this web transversely to the plane of the clip.

Such a cartridge is known from WO 98/05260, for example. Some of the clips received in such a cartridge are very small, e.g. the dimensions lie in the order of 1.5 mm, and therefore the handling of these clips is exceptionally difficult. In the known cartridges the clips are held in the cartridges in such a way that a tongs-like application instrument can grasp the clips upon reaching into the cartridge and then draw them from the cartridge. In this case, a disadvantage with the known cartridges is that the clips are fixed laterally by elastically resilient clamping elements, which only abut in the central region of the web and are removed from the clip upon insertion of an application tool, so that the lateral fixture of the clips is removed upon insertion of the application tool. Therefore, the clip may be tilted or even jammed in the cartridge when the application tool is inserted, and then it is no longer possible to insert the clip into the clip application instrument in the envisaged manner.

The object of the invention is to configure a cartridge of this type such that the clip is held in the cartridge in a fully defined and tilt-free manner in every phase, in particular also when an application tool is inserted into the cartridge.

This object is achieved according to the invention with a cartridge of the type described above in that additional clamping members are provided, which abut the arms laterally at least on one side and are elastically removable from these arms transversely to the plane of the clip, and which are pressed elastically against the arms independently of the clamping members abutting the web.

As a result, the clip is held in the cartridge by elastic clamping members which abut the clip both in the region of the web and in the region of the arms and thus hold said clip at different points. Since the clamping members are elastically removable from the arms independently of one another, the clamping members abutting the arms also remain in their clamping position when an application tool is inserted into the cartridge and thereby removes from the clip the clamping members abutting said clip in the region of the web. The clip is also held securely in this phase by the clamping members abutting the arms. While these clamping members, which normally abut the arms, are also bent elastically downwards upon further insertion of the application instrument, the clip is then already securely disposed in the cartridge and can no longer be tilted.

In a first preferred embodiment it may be provided that the cartridge has clamping members, which are elastically removable from the arms on only one side of the clip, and a fixed contact surface for the clip on the opposite side. With such a construction the clip is pressed against a fixed contact surface by the resilient clamping elements and fixed thereby. In another embodiment it may be provided that clamping members, which abut the clip and are removable therefrom, are provided on both sides of the clip, said clamping members holding the parts of the clip between them in pairs. In this embodiment the resilient clamping members abut the clip on opposite sides so that it is precisely guided and centred between these resilient clamping members. In this case, guidance is achieved by clamping members arranged on opposite sides abutting in pairs at different levels of the clip so that optimum fixture of the clip in the cartridge may be achieved overall.

It is advantageous if the clamping members have spring arms, which at their free end bear pressure surfaces which may be laid against the web or the arms. These pressure surfaces may in particular protrude in the shape of a ball.

In a preferred embodiment it is provided that a respective pressure surface elastically abuts the web at its two end regions, as a result of which the web is held at two points between the clamping members and is thus secured against swivelling.

The two pressure surfaces may be disposed on a web which is supported by two spring arms which maintain a distance between them. Thus, a U-shaped pressure element, on which two pressure surfaces are formed, is obtained.

It is advantageous if the additional clamping members are disposed in the interstice between the spring arms.

In this case, the clamping members abutting the web and the arms may be located in a plane running parallel to the plane of the clip, so that optimum use of the available space results.

In a particularly preferred embodiment it is provided that the cartridge has a U-shaped base body with a web and two legs projecting from these, that the support penetrating between the legs is disposed on the web, and that the clamping members are disposed between the legs and the support.

It is advantageous thereby if the clamping members are in the form of plates and lie close together, so that they form a multiple-part side wall for the interstice between the legs and the support. As a result, a receiving area enclosed on all sides is obtained in the interior of the cartridge which is defined on the narrow sides by the legs and on the broad sides by the plate-shaped clamping members.

In addition, it may be provided that the legs are connected to one another at their free ends by parallel webs, which between them form an insertion opening for a clip and for an application tool. The strength of the cartridge is increased as a result of this.

It is particularly advantageous if the base body, the support, the clamping members and possibly the webs connecting the legs of the base body are made of plastic in one piece.

Several of these cartridges of the same type may be arranged one above the other and joined to one another in the manner of a stack, so that a larger number of clips may be received in such a cartridge stack.

In another preferred embodiment it is provided that several cartridges of the same type are arranged next to one another in one plane.

For example, the cartridges may be arranged parallel to one another in the form of a strip.

In another preferred embodiment, the cartridges are arranged on the outer edge of a disc, in particular a circular disc, and their insertion openings are directed away from one another.

Figure 2:
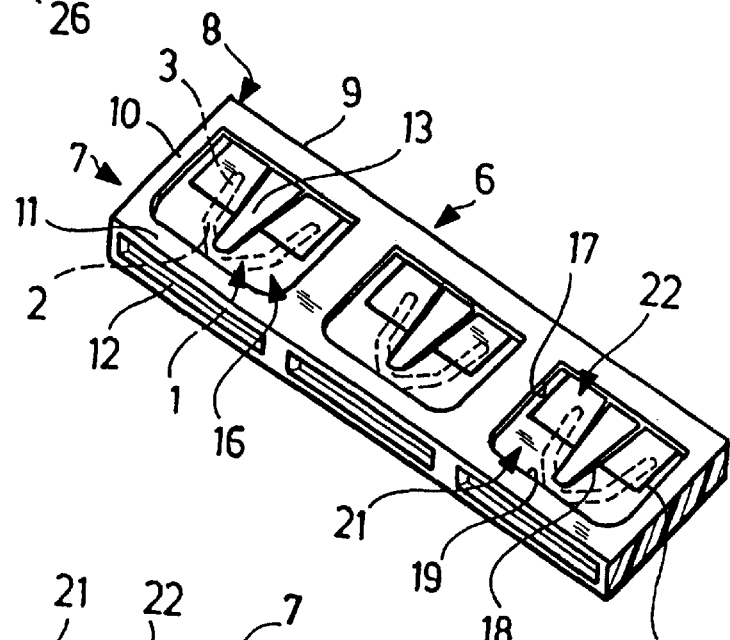
Figure 3:
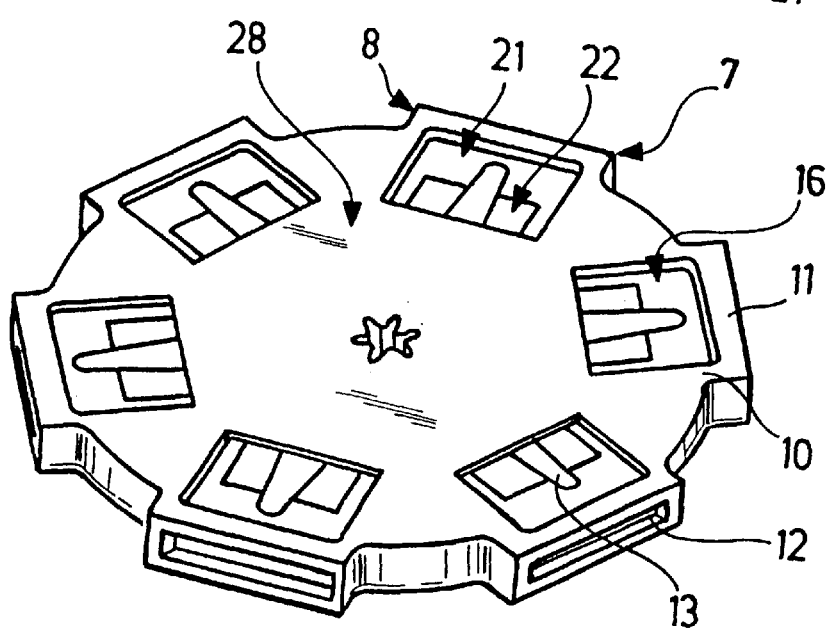

The following description of preferred embodiments of the invention serves to provide a more detailed explanation in association with the drawing:

FIG. 1: shows a clip holder with cartridges arranged one above the other in the form of a stack and an application tool upon insertion into one of the cartridges;

FIG. 2: shows a holder in the form of a strip with several cartridges arranged next to one another;

FIG. 3: shows a holder in the form of a disc with several cartridges arranged along the periphery of the disc;

FIG. 4: is a sectional view taken along line 4—4 in FIG. 1;

FIG. 5: is a sectional view taken along line 5—5 in FIG. 4;

FIG. 6: is a sectional view taken along line 6—6 in FIG. 4;

FIG. 7: is a sectional view of a cartridge taken along line 4—4 in FIG. 1 with a partially inserted application tool;

FIG. 8: is a sectional view taken along line 8—8 in FIG. 7 and

FIG. 9: is a view similar to FIG. 8 with a fully inserted application tool.

The holders shown in the drawing serve to receive U-shaped clips 1, or haemostatic clips which are positioned on blood vessels and compressed in order to constrict the blood vessels. Such clips 1 comprise a web 2 as well as two arms 3 projecting therefrom at the end and lying in the same plane as the web 2. In the embodiment shown in the drawing, the web 2 is angled off in the centre and the arms 3 project from the web 2 such that they diverge slightly towards their free end (FIG. 4). The clips 1 are usually made of a metal tolerable to the body, e.g. special steel or titanium, and may be permanently shaped such that the two arms 3 are brought towards one another and thus receive a vessel to be constricted between them.

Such a clip 1 is applied, for example, by an application tool with two branches 4, which may be moved towards one another and at their free end on the sides facing one another bear longitudinal grooves 5 running parallel to the branches 4 and respectively open towards the opposite branch. The branches 4 in such an application tool are thus pushed over the clip 1 from the web side so that the arms 3 engage into the longitudinal grooves 5 and are pressed against one another slightly, so that such a clip 1 is firmly held between the branches 4. By bringing the branches 4 closer to one another, e.g. by means of a grip part (not shown in the drawing) on the positioning tool, the clip 1 can be compressed in the described manner.

Holders 6, which respectively have a larger number of cartridges 7 of the same construction, are used to store a larger number of such clips 1. Each of these cartridges (FIGS. 4 to 9) comprises a U-shaped base body 8 with a rectilinear web 9 and legs 10 at its ends, which project perpendicular from this and are connected to one another at their free ends by two webs 11 running parallel to one another. An insertion opening 12 results between the two webs 11 which forms an entrance to the interior of the base body.

In the centre of the web 9 a support 13 projects from this which runs parallel to the legs 10 and is not as long as these, so that it terminates at a distance from the webs 11. At its upper end this support 13 has an insertion groove 14 for the central region of the web 2 of the clip 1, this insertion groove 14 running in the longitudinal central plane of the base body 8. The support 13 thereby extends essentially over the entire thickness of the base body 8 and thus divides the receiving area 15 of the base body 8 arranged between the legs 10 into two parts.

The receiving area 15 is closed by two side walls 16 running parallel to the webs 11 and connected to leg 10 along the longitudinal edges thereof, but which otherwise do not have any connection to the base body 8, i.e. narrow gaps 17 or 18 are provided between these side walls 16 and the adjoining legs 10 as well as the support 13, such a gap 19 also being located between the webs 11 and the side walls 16.

Further, the side walls 16 are divided by a gap 20 in such a manner that an outer U-shaped side wall section 21 and two side wall sections 22 spaced from one another are formed which are surrounded by the U-shaped side wall section 21 and the support 13 is located between them (FIG. 4).

The side wall sections 21 and 22 can be resiliently bent outwards out of their plane, on their facing inner sides they bear ball-shaped projections 23 or 24, which respectively lie opposite one another. In this case, two such projections 23 are provided at a distance from one another and adjacent to the free edge 25 of the side wall section 21, while each of the side wall sections 22 respectively bears such a projection 24 on its free end. Thus, both the U-shaped side wall section and the two side wall sections 22 form spring elements, which bear the projections 23 or 24 on their inner side.

The entire cartridge 7 described hitherto is preferably made from plastic in one piece and forms a receiving area 15 for a clip 1.

This is inserted into the receiving area 15 such that its web 2 engages with the angled off central region into the insertion groove 14 of the support 13, while the two arms 3 of the clip 1 plunge into the two parts of the receiving area 15 separated from one another by the support 13. The end regions of the web 2 thereby come to lie between the projections 23 of the side wall section 21, the arms 3 between the projections 24 of side wall sections 22 respectively lying opposite one another. The projections 23 and 24 thus form clamping members, which precisely position and firmly hold the clip 1 in the inserted position when inserted, as is evident from the illustrations of FIGS. 4 to 6.

In order to remove a clip 1 from such a cartridge 7, the two branches 4 of the application tool are inserted into the receiving area 15 through the insertion opening 12 so that they slide over the arms 3 of the clip 1 (FIG. 7). At the beginning of the insertion procedure of the branches 4, these come into abutment against the projections 23 of the side wall section 21 and as a result bend the side wall sections 21 elastically outwards, i.e. the abutment of the projections 23 against the clip 1 is removed. The clip, however, continues to be fixed in its position by the longitudinal grooves 5 of the branches 4, on the one hand, and by the projections 24 on the side wall sections 22, on the other, so that upon further forward movement of the branches 4 the exact positioning of the clip is maintained. During this further insertion, the branches 4 also ultimately press the projections 24 and the side wall sections 22 bearing them outwards (FIG. 9), so that the clip is now held solely in the longitudinal grooves 5 of the branches 4 and in the insertion groove 14 of the support 13. As soon as the branches 4 have been fully inserted, they can be withdrawn from the receiving area 15 together with the clip 1, since the projections 23 and 24 are bent outwards by the branches 4, they can no longer firmly hold the clip 1, this being held between the branches 4 solely by the elasticity of the arms 3 abutting the inner side of the longitudinal grooves 5.

In the embodiment of FIG. 1, several cartridges 7 of the same type are arranged one above the other in the form of a stack, whereby an interstice 26 is maintained between adjacent cartridges 7, the webs 9 of the base bodies 8 being connected to a base plate 27 so that a larger number of cartridges are arranged parallel to one another in such a stack-type holder, each of which being able to receive one clip 1.

In the embodiment of FIG. 2, several cartridges 17 of the same type are arranged next to one another in one plane in the form of a strip, whereby the base bodies 8 of the adjacent cartridges 7 have a joint web 9 and whereby the legs 10 of adjacent base bodies 8 are respectively common to two adjacent base bodies 8. The insertion openings 12 thereby all lie on one side of the strip-type holder 6.

In the embodiment of FIG. 3, several cartridges 7 of the same construction are worked in a circular disc 28, which receives the base bodies 8 of the cartridges 7, which are all constructed in one piece. The orientation thereby is selected such that the insertion openings 12 of the cartridges 7 distributed along the periphery are directed away from one another, i.e. radially outwards.

The present invention relates to the subject matter disclosed in international application PCT/EP 99/10370 of Dec. 24, 1999, the entire specification of which is incorporated herein by reference.

What is claimed is:

1. Cartridge for receiving U-shaped clips (1) having a web (2) and two arms (3) projecting therefrom, with a support (13) abutting the underside of the web (2) and with clamping members, which abut the web (2) laterally at least on one side and are elastically removable from this web (2) transversely to the plane of the clip (2), characterised in that additional clamping members (22, 24) are provided, which abut the arms (3) laterally at least on one side and are elastically removable from these arms (3) transversely to the plane of the clip (1), and which are pressed elastically against the arms (3) independently of the clamping members (21, 23) abutting the web (2).

2. Cartridge according to claim 1, characterised in that the cartridge has clamping members (21, 22, 23, 24), which are elastically removable from the arms on only one side of the clip, and a fixed contact surface for the clip (1) on the opposite side.

3. Cartridge according to claim 1, characterised in that clamping members (21, 22, 23, 24), which abut the clip and are removable therefrom, are provided on both sides of the clip, said clamping members holding the parts of the clip (1) between them in pairs.

4. Cartridge according to claim 1, characterised in that the clamping members have spring arms (21, 22), which at their free end bear pressure surfaces (23 or 24) which may be laid against the web (2) or the arms (3).

5. Cartridge according to claim 4, characterised in that the pressure surfaces (23, 24) protrude in the shape of a ball.

6. Cartridge according to claim 4, characterised in that a respective pressure surface (23) elastically abuts the web (2) at its two end regions.

7. Cartridge according to claim 6, characterised in that the two pressure surfaces (23) are disposed on a web which is supported by two spring arms which maintain a distance between them.

8. Cartridge according to claim 7, characterised in that the additional clamping members (22, 24) are disposed in the interstice between the spring arms.

9. Cartridge according to claim 1, characterised in that the clamping members (21, 22) abutting the web (2) or the arms (3) are located in a plane running parallel to the plane of the clip.

10. Cartridge according to claim 1, characterised in that it has a U-shaped base body (8) with a web (9) and two legs (10) projecting from these, that the support (13) penetrating between the legs (10) is disposed on the web (9), and that the clamping members (21, 23; 22, 24) are disposed between the legs (10) and the support (13).

11. Cartridge according to claim 10, characterised in that the clamping members (21, 22) are in the form of plates and lie close together, so that they form a multiple-part side wall (16) for the interstice (15) between the legs (10) and the support (13).

12. Cartridge according to claim 10, characterised in that the legs (10) are connected to one another at their free ends by parallel webs (11), which between them form an insertion opening (12) for a clip (1) and for an application tool (4).

13. Cartridge according to claim 10, characterised in that the base body (8), the support (13), the clamping members (21, 23; 22, 24) and possibly the webs (11) connecting the legs (10) of the base body (8) are made of plastic in one piece.

14. Cartridge according to claim 1, characterised in that several cartridges (7) of the same type are arranged one above the other and joined to one another in the manner of a stack.

15. Cartridge according to claim 1, characterised in that several cartridges (7) of the same type are arranged next to one another in one plane.

16. Cartridge according to claim 15, characterised in that the cartridges (7) are arranged parallel to one another in the form of a strip.

17. Cartridge according to claim 15, characterised in that the cartridges (7) are arranged on the outer edge of a disc (28) and that their insertion openings (12) are directed away from one another.

\* \* \* \* \*